(12) United States Patent
Sheldon et al.

(10) Patent No.: US 10,307,310 B2
(45) Date of Patent: Jun. 4, 2019

(54) METHODS OF MAKING ABSORBENT CORES AND ABSORBENT PRODUCTS USING SUCH CORES

(71) Applicant: Advanced Absorbent Technologies, LLC, Beaufort, NC (US)

(72) Inventors: Donald A. Sheldon, Beaufort, NC (US); Joseph Howard, Glenmoore, PA (US); William Terenzoni, Jamison, PA (US)

(73) Assignee: Advanced Absorbent Technologies, LLC, Beaufort, NC (US)

( * ) Notice: Subject to any disclaimer, the term of this patent is extended or adjusted under 35 U.S.C. 154(b) by 0 days.

(21) Appl. No.: 15/873,480

(22) Filed: Jan. 17, 2018

(65) Prior Publication Data

US 2018/0140481 A1  May 24, 2018

Related U.S. Application Data

(63) Continuation of application No. 15/625,132, filed on Jun. 16, 2017, which is a continuation of application
(Continued)

(51) Int. Cl.
*A61F 13/532* (2006.01)
*A61F 13/533* (2006.01)
(Continued)

(52) U.S. Cl.
CPC ........ *A61F 13/5376* (2013.01); *A61F 13/534* (2013.01); *A61F 13/5323* (2013.01);
(Continued)

(58) Field of Classification Search
CPC ............ A61F 13/15634; A61F 13/1565; A61F 13/15699; A61F 13/5323; A61F 13/534;
(Continued)

(56) References Cited

U.S. PATENT DOCUMENTS 4,381,783 A    5/1983  Elias
4,695,278 A    9/1987  Lawson
(Continued)

FOREIGN PATENT DOCUMENTS

EP    0401189 A1    12/1990
EP    0724418 B1    8/1996
(Continued)

OTHER PUBLICATIONS

Communication Relating to the Results of the Partial International Search for PCT/US2014/025963 dated Aug. 14, 2014.
(Continued)

*Primary Examiner* — Catharine L Anderson
(74) *Attorney, Agent, or Firm* — Caesar Rivise, PC

(57) ABSTRACT

An absorbent core assembly for use in a product for absorbing a liquid is disclosed. The core assembly has a first section and a second section. The first section is a quilted porous material that contains a slow acting but high absorption capacity SAP therein. The, second section is a quilted porous material that contains a fast acting but lower absorption capacity SAP therein. The first and second sections are in fluid communication with each other, whereupon a liquid which is exposed to the core assembly flows through the first section to the fast acting SAP in the second section to be absorbed quickly and rapidly by the fast acting SAP therein, while the slow acting SAP desorbs or takes liquid away from the fast acting SAP as well as absorbing the liquid itself to thereby trap the liquid in the core assembly.

20 Claims, 2 Drawing Sheets

Related U.S. Application Data

No. 15/042,859, filed on Feb. 12, 2016, now Pat. No. 9,693,911, which is a continuation-in-part of application No. 14/204,616, filed on Mar. 11, 2014, now Pat. No. 9,707,135.

(60) Provisional application No. 61/792,004, filed on Mar. 15, 2013.

(51) Int. Cl.
| | | |
|---|---|---|
| *A61F 13/537* | (2006.01) | |
| *A61G 17/04* | (2006.01) | |
| *A61F 13/534* | (2006.01) | |
| *A61F 13/53* | (2006.01) | |

(52) U.S. Cl.
CPC ........... *A61G 17/04* (2013.01); *A61G 17/042* (2016.11); *A61G 17/047* (2016.11); *A61F 2013/530562* (2013.01); *A61F 2013/530715* (2013.01); *A61F 2013/530722* (2013.01); *A61F 2013/530737* (2013.01); *A61F 2013/530868* (2013.01)

(58) Field of Classification Search
CPC .......... A61F 2013/530481; A61F 2013/53051; A61F 2013/530562; A61F 2013/530715; A61F 2013/530722; A61F 2013/530737; A61F 2013/530868
See application file for complete search history.

(56) References Cited

U.S. PATENT DOCUMENTS

| | | |
|---|---|---|
| 4,743,346 A | 5/1988 | Graham et al. |
| 4,846,823 A | 7/1989 | Enloe |
| 4,994,053 A | 2/1991 | Lang |
| 5,055,103 A | 10/1991 | Nomura et al. |
| 5,163,932 A | 11/1992 | Nomura et al. |
| 5,415,644 A | 5/1995 | Enloe |
| D362,120 S | 9/1995 | Suskind et al. |
| 5,447,508 A | 9/1995 | Numano et al. |
| 5,599,338 A | 2/1997 | Enloe |
| 5,762,641 A | 6/1998 | Bewick-Sonntag et al. |
| 5,788,684 A | 8/1998 | Abuto et al. |
| 5,938,650 A | 8/1999 | Baer et al. |
| 5,977,014 A | 11/1999 | Plischke et al. |
| 6,171,682 B1 | 1/2001 | Raidel et al. |
| 6,258,196 B1 | 7/2001 | Suzuki et al. |
| 6,626,879 B1 | 9/2003 | Ashton et al. |
| 6,689,115 B1 | 2/2004 | Popp et al. |
| 7,112,189 B2 | 9/2006 | Otsubo et al. |
| 7,765,614 B2 | 8/2010 | Takino et al. |
| 7,887,522 B2 | 2/2011 | Roe et al. |
| 7,981,100 B2 | 7/2011 | Takahashi et al. |
| 8,257,331 B2 | 9/2012 | Fujioka et al. |
| 8,257,334 B2 | 9/2012 | Buell et al. |
| 8,622,984 B2 | 1/2014 | Rajala et al. |
| 8,646,506 B2 | 2/2014 | Ukegawa et al. |
| 2003/0109840 A1 | 6/2003 | Dodge, II et al. |
| 2003/0135177 A1 | 7/2003 | Baker |
| 2003/0150551 A1 | 8/2003 | Baker |
| 2005/0075617 A1 | 4/2005 | Vartiainen |
| 2006/0069367 A1 | 3/2006 | Waksmundzki et al. |
| 2006/0153984 A1 | 7/2006 | Suzuki et al. |
| 2006/0184146 A1 | 8/2006 | Suzuki |
| 2007/0032766 A1 | 2/2007 | Liu et al. |
| 2008/0312628 A1 | 12/2008 | Hundorf et al. |
| 2010/0069872 A1 | 3/2010 | Lindstrom |
| 2011/0166540 A1 | 7/2011 | Yang |
| 2013/0102982 A1 | 4/2013 | Nakano et al. |
| 2013/0284362 A1 | 10/2013 | Tsujimoto et al. |
| 2014/0276503 A1 | 9/2014 | Sheldon et al. |
| 2016/0158075 A1 | 6/2016 | Sheldon et al. |

FOREIGN PATENT DOCUMENTS

| | | |
|---|---|---|
| EP | 1257240 B1 | 1/2007 |
| EP | 2444046 A1 | 4/2012 |
| EP | 2679210 A1 | 1/2014 |
| WO | 2011162652 A1 | 12/2011 |

OTHER PUBLICATIONS

International Search Report for PCT/US2014/025963 dated Dec. 3, 2014.

International Search Report for PCT/US2016/021310 dated Oct. 20, 2016.

International Search Report for PCT/US2018/022111 dated Jul. 20, 2018.

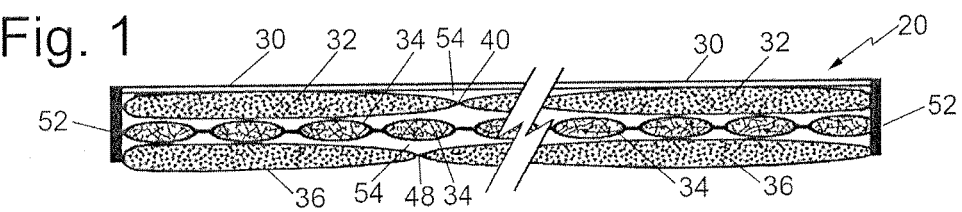
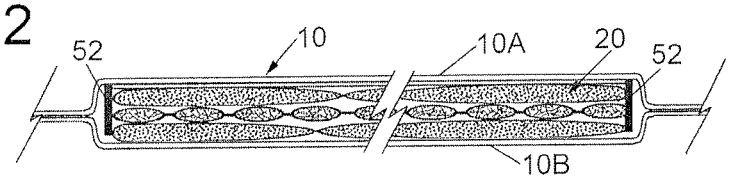
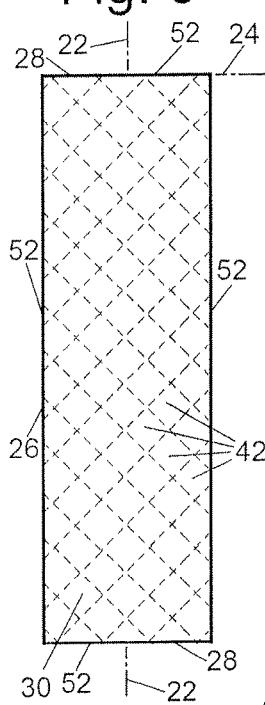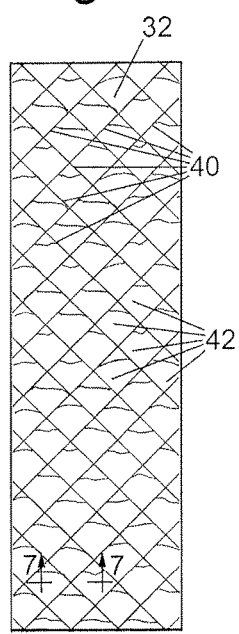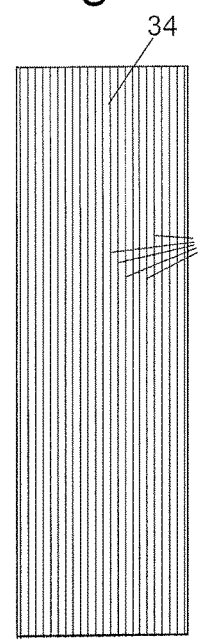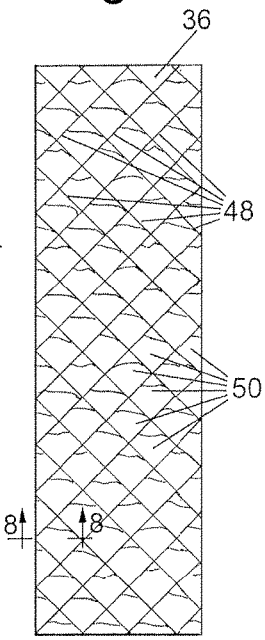
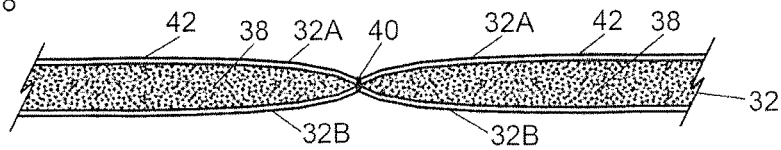
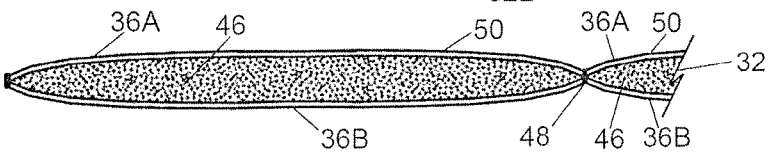

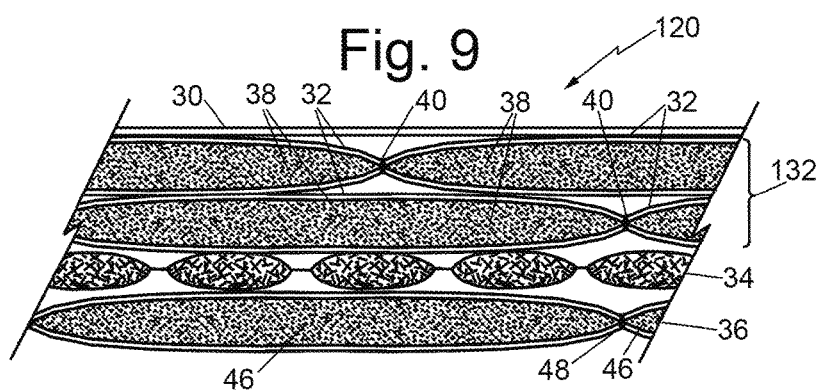
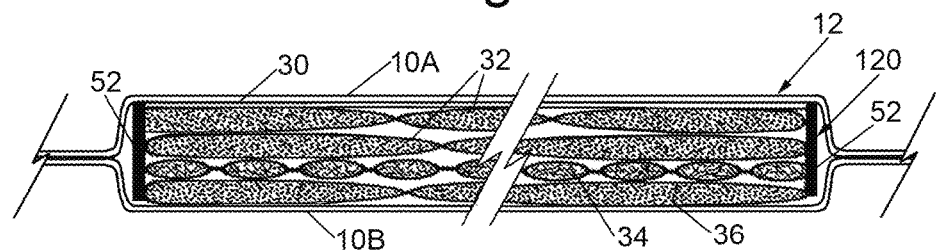

METHODS OF MAKING ABSORBENT CORES AND ABSORBENT PRODUCTS USING SUCH CORES

CROSS-REFERENCE TO RELATED APPLICATIONS

This application constitutes a continuation of application Ser. No. 15/625,132, filed on Jun. 16, 2017, entitled Absorbent Products And Absorbent Core For Use In Same, which in turn is a Continuation of application Ser. No. 15/042,859, filed Feb. 12, 2016, now U.S. Pat. No. 9,693,911, which in turn is a Continuation-In-Part of prior application Ser. No. 14/204,616, filed on Mar. 11, 2014, entitled Disposable Absorbent Article, now U.S. Patent No. 9,707,135, which in turn claims the benefit of Provisional Application Ser. No. 61/792,004, filed on Mar. 15, 2013, entitled Disposable Absorbent Article, all of which are assigned to the same assignee as this invention, and whose disclosures are incorporated by reference herein.

FIELD OF THE INVENTION

This invention relates generally to absorbent cores for absorbent products and methods of making the same.

BACKGROUND OF THE INVENTION

Current adult disposable absorbent products, e.g., adult briefs, that exist in the market today utilize what is known as a fiberized bleached wood fluff pulp and a SAP (Super Absorbent Polymer) mixture for the absorbent core. At low ratios of 30% or less SAP to pulp ratio, the core mixture may or may not be wrapped in an absorbent tissue to prevent the SAP from falling apart or out of the core. At higher levels of SAP at 50% or more, the core must be wrapped to prevent the loose SAP from being shaken out. Also a core adhesive may be added to prevent the heavier SAP particles from being separated from the fluff pulp fibers. This is the most advanced technology of today that is employed in infant sized disposable absorbent products. The pulp fiber in these products is required to rapidly manage the body fluid exudates until the SAP can desorb the fluff fibers to prepare the fluff fibers for the next exudates. For an infant, their body can produce up to 150 ml (grams) of urine and deliver it into the absorbent core over about 70 seconds. This delivery rate starts off rapidly and can achieve approximately 10 to 15 ml per second after the first 5 seconds or so and then trail down to zero. For an adult the amount of exudate is much larger and can easily exceed 300 ml or more delivered over a time period of more than 70 seconds at a rate similar or less than what infants void.

A significant problem with the current absorbent products that contain wood fluff pulp or even wrapped with a tissue or airlaid is in all cases their construction results in a core which feels wet against the body after it has received the voided fluid(s). This wetness feeling is akin to the feeling of wearing a cotton T-Shirt, getting it wet and then continuing to wear the wet cotton T-Shirt long after it should have been changed to a drier shirt. To address this wet feel, almost all current absorbent product designs employ a distancing layer of synthetic fibers on top of the "wet core" as an attempt to create a "feel drier" layer. This synthetic distancing layer is often called a "fluid transfer layer", "fluid acquisition layer", or "acquisition distribution layer (ADL)" and is typically much smaller than the core that it covers, leaving the edges of the core exposed. Moreover, despite their design goal, such fluid acquisition layers only work to a limited degree. In this regard as the exudate leaves the body at 98 degrees Fahrenheit it quickly drops to about 90 degrees Fahrenheit as it enters the core of the absorbent product. This creates a cooling effect when touched by the skin, which may increase during the time worn. If left on for an extended period of time, the wet product will achieve a thermal equilibrium and equilibrate somewhere between room temperature and about 90 degrees Fahrenheit, depending upon ambient temperature and clothes worn. This difference can be further exacerbated depending upon the thermal conductivity of the materials chosen to absorb the exudate. But in all cases current wood pulp fluff absorbent products will feel wet and/or cold to the skin the longer the product is worn.

The current state of the art product design for the synthetic absorbent cores is based upon a synthetic continuous fiber matrix inter-layered with superabsorbent particles (SAP). For example a polypropylene tow fiber similar to tow used in cigarette filter making was chosen. This material is purchased in a continuous form and is pulled out of the box and proceeds into an air trumpet or similar device or the like, to expand the fiber tow matrix. Then SAP particles are intermixed, adhesive is sprayed into the fiber SAP matrix and the entire matrix is wrapped to result in what is the state of the art of current "Pulpless" core technology. This type of core has the major limitations of a slow absorbency rate. That rate is highly dependent upon the SAP chosen and on the adhesive type and amount required to attach the SAP to the tow fiber matrix. For example, if enough adhesive is provided to ensure that the SAP remains in its desired location within the core, that adhesive may limit the SAP's absorbent swelling due to coating part of the SAP particles. If less adhesive is utilized, while it may permit greater swelling and absorption of the exudate by the SAP, it may allow the SAP particles to fall from their positions in the core to the bottom of the crotch area, rendering it heavier and wetter in the crotch area when voided into and less absorbents at the ends.

Another example of current pulpless core technology is gluing the SAP to the back sheet or inside the top or body facing sheet. This bonding process may limit the SAP from being fully expanded and utilized in absorbing the exudate. When bonded in such a matter, the SAP may be also be applied in continuous rows to provide space for the fluid to travel unhindered. Or the SAP may be intermixed with ground wood pulp fibers of similar size to enhanced fluid movement in this inefficient design.

Current SAP limitations require having to choose between a higher absorbent capacity, with the disadvantage of having slower speed, or a faster SAP with less absorbing capacity. If the current SAPs are mixed, the fast acting SAP will very rapidly swell and may "gel-block" the slower acting, but higher absorption capacity SAP. If gel-blocking occurs, it will limit, or even prevent, the higher capacity SAP from desorbing the faster but lower capacity SAP.

In the past a cellulose acetate fiber core with a single SAP has been developed and commercially available, as has a non-SAP version. Current polypropylene filament tow technology has also been used for the absorbent cores. In this regard, such polypropylene tow cores used in the market today make use of round or oval homo-polymer polypropylene fibers, which provide minimal resistance to fluid flow through the SAP/tow fiber matrix, thereby only providing minimal dwell time for the fluid to be absorbed by the SAP.

While such prior art absorbable products containing wood fluff pulp are generally suitable for their intended purposes, they still leave much to be desired. In particular, the thickness of today's disposable absorbent products containing wood fluff pulp and the state of the art in pulp fiberizing technology result in an absorbent product that is significantly thicker than current cotton underwear. This results in a thicker product on the body which may not allow normal clothes or their usual size normal clothing to be worn. In addition the increased thickness of such products results in increased storage, transportation and handling costs and increased retail display space.

In our aforementioned patent application there is disclosed and claimed a disposable absorbent garment, which overcomes many of the disadvantages of art absorbable products containing wood fluff pulp. In particular, that patent application discloses an exemplary absorbent assembly comprising a core formed of a synthetic tow or of synthetic nonwoven layers and having first section comprising a slow acting but high absorption capacity SAP and a second section comprising a fast acting but lower absorption capacity SAP, all of which is wrapped in a wrapper to hold the SAP in place. The absorbent assembly may be quilted and corrugated. The undergarment also includes releasably securable fasteners to enable it to be readily removed and a suspension system to ensure that the garment fits properly and doesn't leak even when holding a large amount of exudate. Odor removal/masking and treatment features may be provided. It addition the undergarment may include a wetness indicator.

The subject invention is directed to an absorbent core assembly which constitutes an improvement over the absorbent cores of our aforementioned patent application. Thus the absorbent core assembly of this invention case be used in the absorbent garment of that patent application, or can be used in any other type of absorbent garment or in other absorbent product designed to quickly and efficiently absorb liquids without leakage therefrom.

SUMMARY OF THE INVENTION

In accordance with one aspect of this invention there is provided a method for making an absorbent core for use in a product used with a being for absorbing and retaining liquids from the body of the being. The method comprises forming a first section of at least one layer of a porous material configured to permit the migration of a liquid therethrough. The at least one layer of the first section is quilted by fixedly secured securement lines to form a plurality of first pockets, each of the first pockets being partially filled with a first volume of a slow acting, but high absorption capacity SAP therein. A second section is formed, with the second section having at least one layer of a porous material configured to permit the migration of a liquid therethrough. The at least one layer of the second section is quilted by fixedly secured securement lines to form a plurality of second pockets, each of the second pockets being partially filled with a second volume of a fast acting but lower absorption capacity SAP therein. The second volume is different than the first volume. The first section is disposed over the second section so that they are in fluid communication with each other, whereupon the resulting core is configured such that a liquid contacting the first section flows through the at least one layer of the porous material of the first section into the first pockets and from there flows through the at least one layer of the second section into the second pockets to be absorbed quickly and rapidly by the fast acting SAP therein, while the slow acting SAP desorbs or takes liquid away from the fast acting SAP as well as absorbing the liquid itself.

In accordance with one preferred aspect of the method of this invention the first volume of slow acting, but high absorption capacity SAP is free in the first pockets, and wherein the second volume of fast acting but lower absorption capacity SAP is free in the second pockets.

In accordance with another preferred aspect of the method of this invention the at least one layer of the first section is formed of a nonwoven material and wherein the at least one layer of the second section is formed of a nonwoven material.

In accordance with another preferred aspect of the method of this invention the first section includes two layers, each of the layers of the first section comprising a plurality of the first pockets containing a portion of the slow acting but high absorption capacity SAP therein. In accordance with another preferred aspect of the method of this invention the pockets are formed by ultrasonically bonding or thermally bonding or adhesively bonding.

In accordance with another preferred aspect of the method of this invention the first pockets are offset with respect to the second pockets. In accordance with another preferred aspect of the method of this invention the method additionally comprises providing a wicking layer disposed between the first and second sections to enhance liquid transfer between the first and second sections.

In accordance with another preferred aspect of the method of this invention the wicking layer comprises an air-laid material.

In accordance with another preferred aspect of the method of this invention the method additionally comprises providing a fluid acquisition layer disposed over the first section.

In accordance with another preferred aspect of the method of this invention the method additionally comprises utilizing the core to form a protective disposable undergarment for the being.

In accordance with another preferred aspect of the method of this invention the method additionally comprises providing a top sheet formed of a material enabling a fluid to pass therethrough, disposing the top sheet over the core, providing a bottom sheet comprising a layer formed of a barrier material to prevent a fluid voided by the being to pass therethrough, disposing the bottom sheet under the core, and assembling the top sheet. The core and the bottom sheet together form the protective disposable undergarment.

In accordance with another preferred aspect of the method of this invention the method additionally comprises providing the protective disposable undergarment with a wicking layer disposed between the first and second sections to enhance fluid transfer from between the first and second sections. In accordance with another preferred aspect of the method of this invention the wicking layer comprises an air-laid material.

In accordance with another preferred aspect of the method of this invention the method additionally comprises providing the protective disposable undergarment with a fluid acquisition layer disposed over the first section, whereupon the fluid acquisition layer is interposed between the top sheet and the first section of the absorbent core.

In accordance with another preferred aspect of the method of this invention the top sheet comprises a non-woven material.

In accordance with another preferred aspect of the method of this invention the bottom sheet comprises a film barrier layer.

DESCRIPTION OF THE DRAWING

FIG. 1 is a cross-sectional view of one exemplary embodiment of an absorbent core assembly constructed in accordance with this invention;

FIG. 2 is reduced size cross-sectional view of the crotch portion of an absorbent garment, e.g., a disposable undergarment or diaper, making use of the core assembly of FIG. 1;

FIG. 3 is reduced size a top plan view of the core assembly of FIG. 1;

FIG. 4 is a reduced size a top plan of one of the layers of the core assembly of FIG. 1;

FIG. 5 is a reduced size top plan view of another one of the layers of the core assembly of FIG. 1;

FIG. 6 is a reduced size top plan view of still another one of the layers of the core assembly of FIG. 1;

FIG. 7 is a greatly enlarged sectional view taken along line 7-7 of FIG. 4;

FIG. 8 is a greatly enlarged sectional view taken along line 8-8 of FIG. 6;

FIG. 9 is a greatly enlarged cross-sectional view of an alternative, and more preferred, embodiment of an absorbent core assembly constructed in accordance with this invention; and FIG. 10 is a reduced size cross-sectional view of the crotch portion of an absorbent garment, e.g., a disposable undergarment or diaper, making use of the core assembly of FIG. 9.

DETAILED DESCRIPTION OF THE PREFERRED EMBODIMENT

Referring now to the various figures of the drawing wherein like reference characters refer to like parts, there is shown in FIG. 1 one exemplary embodiment of an absorbent core assembly 20 constructed in accordance with this invention. The core assembly 20 is designed to absorb liquids that in some way come out of or exit the body of a being, e.g., a person or animal, whether the being is living or dead. The liquid can be an exudate, urine, blood or any other fluid which includes a liquid as a component thereof. The core assembly of this invention has particular utility to be used as a component of a garment, e.g., protective disposable underwear, or a component of a bladder control pad, a sanitary napkin, a disposable diaper, etc. Moreover, it can be used as part of a protective pad for use on a bed or on other furniture or may be used as a part of a coffin liner. It may also be used as a wound dressing. In fact, the core assembly 20 of this invention need not be used to absorb liquids from a being, but can be used for other liquid absorbing purposes. For example, a core assembly constructed in accordance with this invention can be used to absorb aqueous chemical or other liquid spills.

Turning now to FIGS. 1 and 3, the absorbent core assembly 20 as shown therein basically comprises a generally planar body of any suitable peripheral shape. In this exemplary case the core assembly 20 is an elongate rectangle, having a longitudinal axis 22 and a transverse axis 24. The core assembly 20 is composed of at least two layers (to be described below) which are fixedly secured together along their longitudinally extending side edges 26 and their transversely extending end edges 28 by any suitable bonding technique, e.g., ultrasonic bonding, thermal bonding, adhesive bonding, etc.

The first or top layer 30 of the core assembly 20 constitutes an acquisition layer, and is configured to be located confronting the being. This layer, while preferred, is optional such that it can be used for some applications and omitted for other applications. If used, the acquisition layer 30 serves to move the liquid to be absorbed linearly across its area to spread it out across the core assembly. In accordance with one exemplary embodiment of this invention the layer 30 is an airlaid material, such as Shalag STAPPEL40 ADL, STA1PBL40 or STA2PBL38m sold by Shalag US, Inc. or a similar material produced by WPT Corporation or other suppliers of similar ADL nonwoven materials. Such a material is identified by the vendor as being 40 gsm 100% Polyester White. Other similar airlaid acquisition layer materials incorporating Polypropylene, Polyethylene Bi-component fibers or the like used in the industry can be used, with a basis weight ideally of 40 grams per square meter (gsm) +/−10 gsm, although usage as low as 20 gsm or up to 100 gsm is infrequently used. Another alternative is to use a 3D film such as that available from Tredegar Film Products under the trademark AquiDry Plus 120.

The second layer 32, which is sometimes referred to hereinafter as the "first section" of the core is best seen in FIGS. 1 and 4. Thus, as can be seen it is of elongated rectangular shape and is preferably coextensive in size and shape to the first layer 30. Like the layer 30, the first section or layer 32 is also provided to move the liquid linearly. However, unlike the first layer 30, the first section or layer 32 is a required layer. It is constructed using high capacity, but slow absorbing SAP particles 38, encapsulated between two sheets or webs 32A and 32B as best seen in FIG. 7. In accordance with one exemplary embodiment of this invention the sheets or webs are formed of a non-woven, liquid pervious material, e.g., 15 +/−5 grams per square meter basis weight hydrophilic spunbond nonwoven polypropylene or the like. One particularly suitable nonwoven is available from PGI Nonwovens under code # B0305 white SBPP hydrophilic polypropylene spunbond. At minimum the upper body side layer 32A is hydrophilic where the bottom layer 32B, may be similar for ease of manufacturing. Alternatively, it could be hydrophobic or an apertured film. Like the top layer 30, the layer 32 is also of elongated rectangular shape and preferably is coextensive is size and shape with the top layer 30.

The formation of the first section or layer 32 of the core assembly 20 is achieved by fixedly securing the webs or sheets 32A and 32B to each other by intersecting seal lines 40 to thereby result in a quilted subassembly having a plurality of compartments or pockets 42 located between the intersecting seal lines. The quilted nature of the first section 32 renders the SAP 38 particles of that section resistant to migration with respect to the core assembly and thus obviates the need for adhesives to bond to the SAP particles to prevent their migration. The seal lines 40 can be made by any suitable technique, e.g., ultrasonic welding, thermal welding, adhesive securement, etc.

One exemplary embodiment of the first section 32 constitutes a diamond-like pattern of the intersecting lines 40 wherein each pocket 42 is of a square shape and is approximately 1.5 cm by 1.5 cm. with the width of each of the intersecting seal lines 40 being approximately 1 mm.

Each pocket 40 of the first section contains free high capacity, but slow absorbing SAP, with each pocket being filled to less than half of its capacity, and preferably within the range of approximately one third to one quarter (or even slightly less) of its capacity. In accordance with one exemplary embodiment of this invention the high capacity, but slow absorbing SAP 38 can be Aqua Keep type SA605, SA60SX11 or Aqua Keep type SA55SX11 available from Sumitomo Seika Chemicals Co., Ltd., or can be BASF T-9400, BASF T-9600 or BASF T-9900 available from BASF Corporation, or any other suitable SAP. Preferably the SAP 38 should have a vortex time of at least, e.g., approximately 40 to 60 or more seconds.

As is known in the art the term "vortex time" represent the amount of time that it takes SAP which is mixed with water in a vessel by a spinning stirrer to form a gel to stop the spinning stirrer.

Each pocket 40 encapsulates approximately 0.07 to 0.08 grams of SAP, or approximately 100 grams of SAP per square meter. The partial filling of the pockets with the high capacity, but slow absorbing SAP 38 serves to allow for the expansion and swelling of the SAP when in contact with the liquid to be absorbed, e.g., urine. If the pockets 40 were filled with significantly more SAP 38, such as greater than 0.32 grams per pocket, the SAP 38 would be constrained in its ability to swell and thus unable to absorb additional fluid. In some instances it may be appropriate to underfill the pockets employing 0.04 grams or even 0.02 grams to ensure maximum utilization at a slightly reduced capacity. It should be pointed out that other size pockets than those described above are contemplated. For example, one can increase the amount of SAP 38 per pocket 40 by employing larger pockets. In each case, the ratio of SAP 38 to the pocket size should not exceed approximately 0.4 grams per 4 square centimeters per pocket. If larger pockets are contemplated, then the same ratio of weight per unit area should be applied.

The third layer 34 of the core assembly 20 is also optional, but desirable, and is shown best in FIGS. 1 and 5. This layer serves to aid in transporting liquid by wicking or the like. In particular the layer 34 is configured to aid in allowing the liquid to linearly wick so that it assists in moving the liquid to be absorbed, e.g., urine, from the central middle area of the core where the liquid is first insulted to the ends of the core where that liquid may not fully reach and to allow that liquid to pass through it into the fourth or bottom layer. In the exemplary embodiment, the wicking layer is a fluid wettable hydrophilic layer containing absorbent tissue, cotton or the like ranging from approximately 50 to 200 gsm. One particularly suitable material for the wicking layer 34 is available from Domtar/EAM Corporation under the trademark Nova Thin and is described as White Fibrous Web of 100 gm basis weight. The layer 34 has a corduroy or corrugated embossing pattern that is employed to further assist wicking. The corrugations or corduroy pattern is formed by a plurality of closely disposed parallel seal lines 44 made by any suitable technique, e.g., ultrasonic welding, thermal welding, adhesive securement, etc. The wicking layer is also of elongated rectangular shape, but preferably of a smaller size than the layers 30 and 32 and is not bonded (for a reason to be described later). Moreover, the wicking layer 34 may be in the form of plural layers to provide the desired wicking properties. The wicking layer may also have visible holes, of 1 mm in size or larger, added to further enhance fluid pass through.

The fourth or bottom layer 36 is also a required layer and is sometimes referred to hereinafter 36 is preferably coextensive in size and shape to the first section 32. The second section 36 is configured to be disposed away from the being and is constructed somewhat similarly to the first section 32. To that end, the second section is in the form of fast acting but lower absorption capacity SAP particles 46 encapsulated between two sheets or webs 36A and 36B of a non-woven, liquid pervious material, e.g., 15 +/−5 gsm basis weight polypropylene like that used in the first section 32. Like the webs or sheets of the first section, the webs or sheets 36A and 36B of the second section are fixedly secured to each other by intersecting seal lines 48 to form a quilted subassembly having a plurality of compartments or pockets 50 located between the intersecting seal lines. The seal lines are formed by any suitable technique, e.g., ultrasonic welding, thermal welding, adhesive securement, etc. Each pocket 50 contains a portion of the fast acting but lower absorption capacity SAP 46 therein, with each pocket being filled to less than half of its capacity, and preferably within the range of approximately one third to one quarter (or even slightly less) of its capacity. In accordance with one exemplary embodiment of this invention the fast acting but lower absorption capacity SAP 46 can be Aqua Keep type SA10 or Aqua Keep type BA40B available from Sumitomo Seika Chemicals Co., Ltd., or the like. Those products have a very fast vortex time, e.g., approximately 4 to 10 seconds. It is preferred that the SAP 46 of the second section have a vortex time of less than 10 seconds, but longer times may be suitable, depending upon the application. In any case, like the first section, the quilting of the second section renders the SAP 46 of the second section resistant to migration with respect to the core assembly without requiring adhesives to bond to the superabsorbent particles to prevent their movement or migration.

The sheets or webs 36A and 36B of the second section 36 are ultrasonically bonded in a diamond pattern pocketing like the first section, with each pocket 50 being approximately 1.5 cm by 1.5 cm square and with the width of the intersecting seal lines being approximately 1 mm in width. Other thermal techniques may also be employed. Each pocket 50 encapsulates approximately 0.02 to 0.08 gm of the SAP 46, or approximately 100 gsm per square meter. In this construction adhesives to bond to the superabsorbent particles to prevent their movement or migration are not required, nor desired.

The pockets 50 are only partially filled to allow for the expansion and swelling of the superabsorbent polymers when in contact with the fluid. If the pockets were filled with significantly more superabsorbent polymer particles 46, such as greater than 0.32 gm per pocket, the SAP particles would be constrained in their ability to swell and thus unable to absorb additional fluid. However, other size pockets may be contemplated to increase the amount of SAP per pocket by employing larger pockets. In each case, the ratio of SAP 46 to the pocket size should not exceed approximately 0.4 gm per 2.25 square cm per pocket. If larger pockets are contemplated, then the same ratio of weight per unit area should be applied.

As best seen in FIGS. 1 and 3, the four layers 30, 32, 34 and 36 are fixedly secured together along their marginal edges by respective seal lines 52 to form a composite assembly. The seal lines 52 are formed by any suitable technique, e.g., ultrasonic welding, thermal welding, adhesive securement, etc. The most desirable process is to ultrasonically bond the four layers together with a two mm wide intermittent bond pattern running down the sides of the four layer composite core and spaced about one cm from each edge, e.g., somewhat like a railroad track with approximately four bond points or bars per cm. To assist in bonding the wicking layer 28 is narrower than the total composite core. For example if the composite core is 100 mm wide, the non-thermal bondable wicking layer will be no wider than 75 to 80 mm in width. This is done to assist ultrasonically bonding the three fusible layers 30, 32 and 36, encapsulating the non-fusible layer 34 between them. An alternative construction would be to use an adhesive either lightly sprayed or slot coated to allow the fluid to travel through the construct unhindered.

The absorbent core assembly 20 is arranged to be located in a garment, to be described shortly, such that the layer 32 (the first section of the core) constitutes a body-facing side confronting the being and the layer 36 (the second section of the core) constitutes a remote-facing side disposed away from the being, whereupon a liquid voided, exuded or otherwise emanating from the body of the being flows through the first section to the fast acting SAP in the second section to be absorbed quickly and rapidly by the fast acting SAP therein, while the slow acting SAP desorbs or takes liquid away from the fast acting SAP as well as absorbing the liquid itself. The wicking layer 30 serves to enhance the fluid transfer from the lower faster absorbent layer 36 into the upper slower absorbent layer 32.

In order to improve fluid movement through the entire composite absorbent core, it is preferred that the embossed pockets 42 and 50 are not aligned directly with respect to each other. Rather they are offset in the X direction (parallel to the longitudinal axis 22) and/or in the Y direction (parallel to the transverse axis 24). This allows for improved fluid migration not only in the X/Y direction, but also in the Z direction, i.e., perpendicular to the plane of the core assembly. However, if desired, e.g., in the interest of ease and simplicity of manufacturing the core, reduced capital costs and concomitant consumer savings, the embossed pockets may be directly aligned under each layer and under each other.

As should be appreciated by those skilled in the art the quilted construct of a core assembly 20 constructed in accordance with this invention functions via what can be called a "compartment spill over phenomena". In particular, the liquid to be absorbed when brought to the each section of the core will fill up the SAP contained in a compartment (pocket) of that section, whereupon the compartment and the SAP in it will swell. Once the SAP in that compartment is fully utilized (e.g., has swelled to its maximum), the liquid then "spills over" to the adjacent compartments. As mentioned above, the ultrasonically formed SAP diamond shaped compartments 44 and 50 of the first section 32 and the second section 36, respectively, have approximately a 1 mm space between them as a result of the width of their respective intersecting seal lines 40 and 48. This aids in liquid movement, along the voids 54 in the core assembly adjacent those seal lines as shown in the cross-sectional view of FIG. 1. As will be appreciated by those skilled in the art, the wicking layer 34 also enhances liquid movement and does the unaligned nature of the compartments or pockets. The addition of a topmost body side layer, commonly referred as an acquisition layer, transfer layer or distancing layer further aids fluid transfer to assist fluid in the spill over from one SAP containing compartment or pocket to the next.

It should be pointed out at this juncture that if a higher capacity absorbent core is desired, one or more additional SAP layers like those of the first section and/or the second section could be added to the construct. In addition, a second wicking layer could be added between the SAP absorbent layers, if desired.

Turning now to FIG. 9, there is shown a more preferred core assembly 120 constructed in accordance with this invention. The core assembly 120 is of similar construction to the core 20, except that the first section of the core assembly 120 is made up of two layers and instead of a single layer 32. In the interest of brevity the components of the core assembly 120 which are common with the core assembly 20 will be given the same reference numbers and the details of their construction, assembly and operation will not be reiterated. Thus, as can be seen the core assembly 120 includes an optional top layer 30, a first section 132 made up of two layers 32, a wicking layer 34 and a second section 36. Each of the two layers 32 making up the first section 132 is constructed in a similar manner to the layer 32 of the core assembly 20. In particular, each layer 32 is constructed using high capacity, but slow absorbing SAP particles 38, encapsulated between two sheets or webs 32A and 32B as best seen in FIG. 7. Each sheets or web are formed of a non-woven, liquid pervious material, e.g., 15 +/−5 grams per square meter basis weight hydrophilic spunbond nonwoven polypropylene or the like, such as that available from PGI Nonwovens under code # B0305 white SBPP hydrophilic polypropylene spunbond. The formation each layer 32 of the first section 132 of the core assembly 120 is achieved by fixedly securing the webs or sheets 32A and 32B to each other by intersecting seal lines 40 to thereby result in a quilted subassembly layer having a plurality of compartments or pockets 42 located between the intersecting seal lines. The two layers 32 of the first section 132 are superimposed over each other such that their pockets 42 are not aligned longitudinally or transversely. By making use of two layers of the first section, the core assembly 120 can use less SAP in each of the pockets 42 of the first section than is used in the pockets 42 of the first section of the core assembly 20. For example, the amount of SAP 38 in each of the pockets 42 of the two layers may be in the range of one third to one quarter or less than the capacity of the pocket. This configuration provides sufficient room for the SAP 38 to expand in the pockets 42 so that it can be fully utilized to desorb the SAP 46 from the second section 36. While it is desirable to use the least amount of SAP 46 in the pockets 42 of the first section for economic reasons, the amount used must be able to be fully utilized to achieve the desired absorption rate and capacity. Thus, is preferred that the SAP 42 in each of the two layers of the first section 132 is within the aforementioned desired range of pocket fullness and that the SAP has a vortex time of at least 60 seconds to be able to fully desorb the liquid from the second section 32. Moreover, that configuration maximizes SAP performance and enables efficient and effective transfer of liquid introduced into the core assembly through each of the two layers of the first section into the second section, without any tendency for the SAP 38 of the first section to impede the flow of liquid into the second section 32 as could result from "gel blocking". As is known "gel blocking: occurs when the surface of the SAP in a section that comes into contact with the liquid first swells and blocks the lower levels of SAP of that section from fully absorbing to their maximum capacity. Thus, by using less SAP in each pocket 42, but by using more pockets via the two layer construction of the first section 132, the occurrence of gel blocking is minimized if not eliminated. Thus, the liquid introduced into the core assembly can quickly pass through the first section to be wicked into the second section, where it is quickly absorbed by the SAP of the second section, and from whence that liquid can go back to the first section where that liquid is slowly absorbed, thereby desorbing the second section, so that all of the liquid is trapped in the core assembly to keep the user of the core dry.

While the preferred embodiment of the core 120 includes two layers in the first section 132, that is merely exemplary. Thus, it is contemplated to use more than two layers in that section, with the pocket sizes and capacity being adjusted accordingly. However it should be recognized that there is an additional cost in using more than two layers for the first section, e.g., the cost of the non-woven material encapsulating the additional layer(s). Moreover, if desired the second section 36 may be made up of multiple quilted layers.

Further still, it is also contemplated that the subject invention can use less expensive inorganic additives to maximize SAP performance. Since the goal of the core of this invention is to allow all the SAP particles of each section to achieve their maximum absorbent capacity, inorganic additives such as high porosity Zeolite's, Upsalite, microspheres or other inorganic materials that do not swell or add to the gel blocking phenomena may be included with the SAP of the core. Another approach in lieu of the use of such inorganic additives, or an additional approach to using such additives, is to utilize an acquisition layer, such as a 40 gm Shalag ADL or similar materials from Shalag US, Inc. or similar materials available from WPT Corporation or others may be disposed underneath the second section of the core.

Absorbent cores constructed in accordance with this invention, such as those described above or variations thereof, could be used in lieu of an absorbent core that is employed in current existing absorbent products. For example, core assemblies constructed in accordance with this invention can be used in adult incontinence products (e.g., briefs, panties, pads, etc.), infant absorbent garments (e.g., diapers), sanitary napkins, a feminine napkins, panty liners, or any other product arranged to be worn by a being to absorb liquids from the being.

In FIG. 2 there is shown a cross-sectional view of the crotch region of an exemplary product, e.g., an adult incontinent brief, 10 making use of a core assembly 20. The brief 10 includes a top sheet 10A and a bottom sheet 10B. The top sheet may be a non-woven material like that typically used in products of this kind. The bottom sheet 10B constitutes a barrier layer, e.g., constitutes a film of polyethylene or polypropylene, also like that typically used in products of this kind to insure that none of the liquid leaks out the brief. Located between the top and bottom sheets 10A and 10B, respectively, is the core assembly 20.

In FIG. 10 there is shown a cross-sectional view of the crotch region of another exemplary product, e.g., also an adult incontinent brief 12, making use of a core assembly of this invention, in this case core assembly 120. The brief 12 is of similar construction to the brief 10, except for the use of the core assembly 120 in lieu of the core assembly 20. In the interest of brevity the components of the brief 12 that are common with the brief 10 will be given the same reference numbers and the details of their construction, assembly and operation will not be reiterated. Thus, it can be seen that the brief 12 includes a top sheet 10A and a bottom sheet 10B. The top sheet may be a non-woven material and the bottom sheet 10B may be a barrier film of polyethylene or polypropylene, like that typically used in products of this kind. Located between the top and bottom sheets 10A and 10B, respectively, is the core assembly 120.

Other alternative constructs for absorbent core assemblies of this invention are also contemplated. For example, in order to create the maximum absorbent capacity in a product with improved surface dryness, such as the adult incontinent briefs described above, one can apply one or more layers of a quilted SAP containing nonwoven layer over the top of an airlaid or fluff mat, but under the top sheet of the brief. The SAP needs to absorb slower than the pulp containing-mat underneath it to act as a surface dryness reservoir. In this construct, the SAP layer may be smaller than the airlaid or fluff mat. In order to increase speed of absorbency and total capacity of the pad of that garment, one or more layers of a quilted SAP containing nonwoven layer under the bottom of an airlaid or fluff mat, but above the polyethylene or polypropylene barrier film. The SAP needs to absorb faster, or at least as fast, as the pulp containing mat above it to act as a fluid containment layer.

Garments or other absorbent products making use of a quilted SAP containing nonwoven layer over the top of an airlaid or fluff mat, but under the top sheet as described above, may be of similar size, smaller and may be shaped other than being of a rectangular shape like the core assemblies described above. Similarly, absorbent core assemblies may make use of one or more quilted SAP layers under airlaid or fluff mat, but above the polyethylene or polypropylene barrier film as described above, may be provided and may be of similar size, smaller or even shaped other than being of a rectangular shape.

As mentioned above, the subject invention also contemplates use of the absorbent core assembly in pad for disposition on a bed or other article of furniture to protect the bed or other article from liquids, e.g., urine, or may be in the form of a coffin liner to protect a coffin from liquids exiting the body of a corpse disposed thereon. For either of such applications, the pad/liner may be in the form of a unitary composite composed of four layers. The first layer constitutes the top sheet of the pad and is configured to be in contact with the being's body and may be composed of a polypropylene spunbond or the like, usually 15 gsm +/−5 gsm. Alternatively, it may be of a higher basis weight or a synthetic through-air bonded carded web. The next layer may be a single layer or multiple layers and forms the first section of the pad/liner. The first section is in the form of a high capacity but slow absorbing layer of SAP particles encapsulated between two layers of 15 +/−5 grams per square meter polypropylene or the like material in a quilted pocketed configuration. The pockets contain free SAP and are filled at less than 20%, and preferably in the range of approximately 1% to 5%. This layer serves to allow fluid to pass therethrough. The third layer constitutes the second section of the pad is also required. It may be a single layer or multiple layers. In any case it contains a fast absorbing SAP with a vortex time of no more than about 10 seconds. This fast absorbing layer of SAP is encapsulated between two layers of 15 +/−5 grams per square meter polypropylene or the like material in a quilted pocketed style. The pockets contain free SAP and are filled at less than 20% and preferably in the range of approximately 1% to 5%. The construction of this layer enables it to rapidly capture the fluid and pull it away from the being's body. Then the layers of SAP above this layer may desorb this layer due to their higher capacity. The fourth layer is a barrier layer composed of a barrier film or film laminate and serves to prevent leakage onto the bedding or other furniture on which the pad/liner is disposed.

The four layers of the pad/liner are preferably sealed around the entire perimeter of the pad/liner by ultrasonic bonding, thermal bonding or by adhesives in a continuous or intermittent pattern or the like. It also may have the layers or parts therein bonded to each other with adhesives or in spots using known techniques such as ultrasonic bonding, thermal bonding, etc.

Instead of using the above composite as a unitary pad structure, it may also be used in place of airlaid or pulp fluff mats used in the current under-pads to retrofit such under-pads. To that end a composite structure in accordance with this invention can be provided. That structure includes only the second and third layers as discussed above which would be used as an insert into current processes in place of their current airlaid or SAP/airlaid materials or pulp or pulp/SAP mats. Further a single pocketed layer of the SAP like that used in the subject invention can be used either alone or in conjunction with airlaid or pulp/SAP mats as follows. A single high capacity SAP pocked layer may be added on top of a current absorbent core for added capacity. This structure would also provide the advantage of increased dryness and total capacity. A single fast absorbing SAP pocked layer may be added under the current absorbent core to increase the speed of the management of fluid. Such a structure would also increase the speed of absorbency and total capacity.

All of the foregoing under-pads can be readily produced as a continuous roll of absorbent pads on a roll that could be more easily used like paper towels on a roll. To that end, each under-pad can be manufactured so that it is attached to the corresponding next under-pad through a series of weak perforations or the like.

As should be appreciated from the foregoing the cores of this invention as described above make use of at least two sections, each of which is of a quilted construction including plural pockets. Moreover, each of the pockets is hollow and is partially filled with SAP. The SAP may be in the form of particles or fibers or any other form of SAP which is free or unsecured. The pockets serve to hold the SAP therein to prevent migration of the SAP through the core. It is, however, contemplated that for some applications an adhesive could be used in the pockets to thereby hold the SAP in place. That alternative configuration provides an additional means, in addition to the pockets, for preventing the SAP from migrating through the core.

Without further elaboration the foregoing will so fully illustrate our invention that others may, by applying current or future knowledge, adopt the same for use under various conditions of service.

We claim:

1. A method of making an absorbent core for use in a product used with a being for absorbing and retaining liquids from the body of the being, said method comprising:
   forming a first section of at least one layer of a porous material configured to permit the migration of a liquid therethrough;
   quilting said at least one layer of said first section by fixedly secured securement lines to form a plurality of first pockets, each of said first pockets having a first volume and being partially filled with a first volume of a slow acting, but high absorption capacity SAP therein, said first volume of said slow acting, but high absorption capacity SAP being less than half of said first volume of said first pockets;
   forming a second section of at least one layer of a porous material configured to permit the migration of a liquid therethrough;
   quilting said at least one layer of said second section by fixedly secured securement lines to form a plurality of second pockets, each of said second pockets having a second volume and being partially filled with a second volume of a fast acting but lower absorption capacity SAP therein, said second volume of said fast acting but lower absorption capacity SAP being less than half of said second volume of said first pockets, said second volume of said fast acting but lower absorption capacity SAP being different than said first volume of said slow acting, but high absorption capacity SAP;
   disposing said first section over said second section so that they are in fluid communication with each other, whereupon the resulting core is configured such that a liquid contacting said first section flows through said at least one layer of said porous material of said first section into said first pockets and from there flows through said at least one layer of said second section into said second pockets to be absorbed quickly and rapidly by said fast acting SAP therein, while said slow acting SAP desorbs or takes liquid away from said fast acting SAP as well as absorbing said liquid itself.

2. The method of claim 1, wherein said first volume of slow acting, but high absorption capacity SAP is free in said first pockets, and wherein said second volume of fast acting but lower absorption capacity SAP is free in said second pockets.

3. The method of claim 1, wherein said at least one layer of said first section is formed of a nonwoven material and wherein said at least one layer of said second section is formed of a nonwoven material.

4. The method of claim 1, wherein said first section includes two layers, each of said layers of said first section comprising a plurality of said first pockets containing a portion of said slow acting but high absorption capacity SAP therein.

5. The method of claim 1, wherein said pockets are formed by ultrasonically bonding or thermally bonding or adhesively bonding.

6. The method of claim 1 wherein said first pockets are offset with respect to said second pockets.

7. The method of claim 1 additionally comprising providing a wicking layer disposed between said first and second sections to enhance liquid transfer between said first and second sections.

8. The method of claim 7 wherein said wicking layer comprises an air-laid material.

9. The method of claim 1 additionally comprising providing a fluid acquisition layer disposed over said first section.

10. The method of claim 1 additionally comprising utilizing said core to form a protective disposable undergarment for the being.

11. The method of claim 10, wherein said method additionally comprises:
   providing a top sheet formed of a material enabling a fluid to pass therethrough;
   disposing said top sheet over said core;
   providing a bottom sheet comprising a layer formed of a barrier material to prevent a fluid voided by the being to pass therethrough;
   disposing said bottom sheet under said core; and
   assembling said top sheet, said core and said bottom sheet together to form said protective disposable undergarment.

12. The method of claim 11, additionally comprising providing said protective disposable undergarment with a wicking layer disposed between said first and second sections to enhance fluid transfer from between said first and second sections.

13. The method of claim 12 wherein said wicking layer comprises an air-laid material.

14. The method of claim 11, additionally comprising providing said protective disposable undergarment with a fluid acquisition layer disposed over said first section, whereupon said fluid acquisition layer is interposed between said top sheet and said first section of said absorbent core.

15. The method of claim 11, wherein said top sheet comprises a non-woven material.

16. The method of claim 11, wherein said bottom sheet comprises a film barrier layer.

17. The method of claim 15, wherein said bottom sheet comprises a film barrier layer.

18. The method of claim 1, wherein said first volume of said slow acting, but high absorption capacity SAP is within the range of approximately one third to one quarter of said first volume of said first pockets.

19. The method of claim 1, wherein said second volume of said fast acting but lower absorption capacity SAP is within the range of approximately one third to one quarter of said second volume of said first pockets.

20. The method of claim 18, wherein said second volume of said fast acting but lower absorption capacity SAP is within the range of approximately one third to one quarter of said second volume of said first pockets.

\* \* \* \* \*